United States Patent
Prosst et al.

[11] Patent Number: 5,814,056
[45] Date of Patent: Sep. 29, 1998

[54] SEAL

[75] Inventors: Rüdiger L. Prosst, Tübingen; Klaus Roth, Ofterdingen; Gerhard Buess; Marc O. Schurr, both of Tübingen, all of Germany

[73] Assignee: Willy Rüsch AG, Kernen-Rommelshausen, Germany

[21] Appl. No.: 790,663

[22] Filed: Jan. 30, 1997

[30] Foreign Application Priority Data

Jul. 18, 1996 [DE] Germany .................. 196 28 909.2

[51] Int. Cl.$^6$ .................................................. A61B 17/04
[52] U.S. Cl. .......................... 606/151; 606/228; 24/16 PB
[58] Field of Search ..................................... 606/224, 228, 606/232, 151, 213, 216; 24/16 PB

[56] References Cited

U.S. PATENT DOCUMENTS

| | | | |
|---|---|---|---|
| Re. 31,541 | 3/1984 | Wood | 24/16 PB |
| 3,514,810 | 6/1970 | Westergren | 24/16 PB |
| 3,570,497 | 3/1971 | Lemole | 24/16 PB |
| 4,050,100 | 9/1977 | Barry | 606/151 |
| 4,069,825 | 1/1978 | Akiyama | 606/174 |
| 4,730,615 | 3/1988 | Sutherland et al. | 606/151 |
| 4,955,913 | 9/1990 | Robinson | 606/228 |
| 5,123,913 | 6/1992 | Wilk et al. | 606/224 |
| 5,196,022 | 3/1993 | Bilweis | 606/144 |
| 5,207,694 | 5/1993 | Broome | 606/148 |
| 5,520,691 | 5/1996 | Branch | 606/72 |

FOREIGN PATENT DOCUMENTS

| | | |
|---|---|---|
| 2651113 | 3/1991 | France . |
| 2519109 | 11/1975 | Germany . |
| 2617856 | 5/1977 | Germany . |

Primary Examiner—Gary Jackson
Attorney, Agent, or Firm—Paul Vincent

[57] ABSTRACT

A seal 10 comprises a bushing 11 and a thread 12, wherein the bushing 11 has a first lumen 15 and a second lumen 16. The lumina 15 and 16 extend along the entire length of the bushing 11. The thread 12 can be introduced at one end into the second lumen 16 and has a swelling 21 at the free end which prevents reintroduction and travel of the end of the thread through the second lumen 16. The thread 12 can be introduced into the first lumen 15 via its other free end and pushed through first lumen 15. Enlargements 20 are formed on the thread 12 having a size preventing introduction into the first lumen 15 without the exercise of force. The bushing 11 and the thread 12 are manufactured from a flexible material having a stable shape. When the enlargements 20 are pulled into the first lumen 15, the bushing 11 bends and seats on e.g. tissue to be ligated. When the enlargements 20 are completely pulled into the first lumen 15, the seal 10 is permanently closed. Subsequent thereto the thread 12 is cut-off outside of the seal 10. The seal 10 can be applied using conventional knot-displacers.

8 Claims, 2 Drawing Sheets

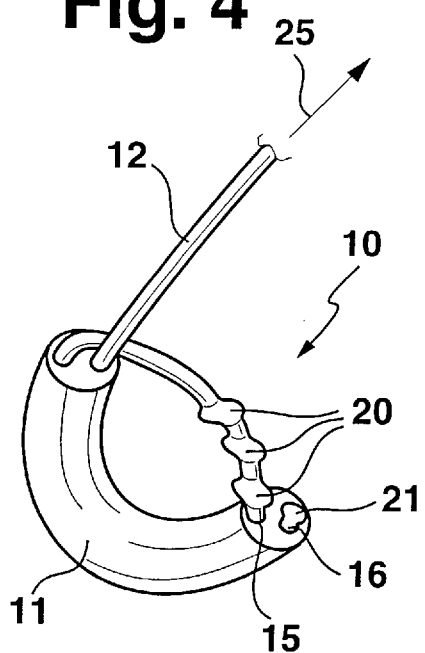
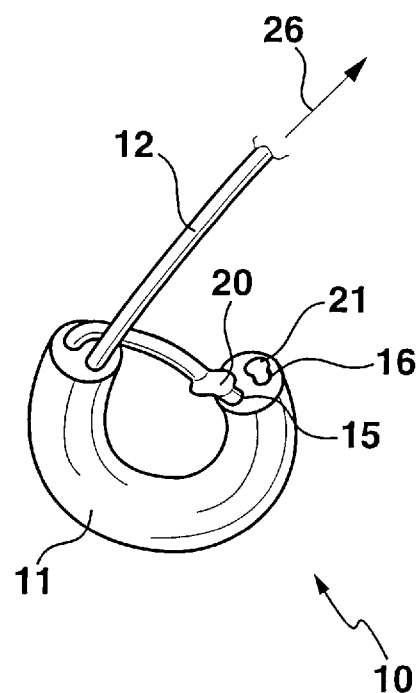
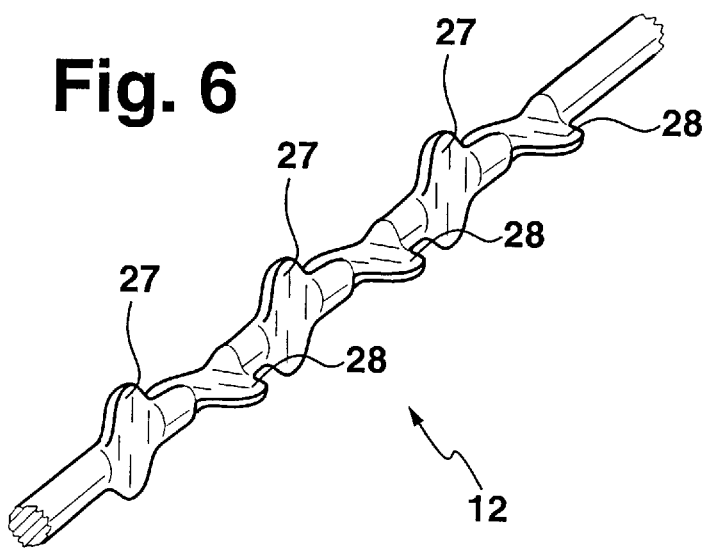

SEAL

BACKGROUND OF THE INVENTION

The invention concerns a seal, e.g. to replace a knot for ligatures and/or sutures, which can be, in particular, advantageously used in minimal invasive surgery. Safe and reliable knotting is of decisive importance for the ligature and the suture. Towards this end, special techniques are necessary in endoscopic surgery. Intracorporeal and extracorporeal knotting techniques can be used. However, both methods require a certain amount of dexterity which, for example, can be attained through practice on phantoms.

Preknotted endoligatures based, for example on a principle similar to that of Yoon-rings are commercially available along with a plastic knot-displacer. A ligature loop of this type comprises a loop having its long end disposed in a knot-displacer. In order to be able to pull back the end of the thread, the end of the knot-displacer is broken-off. The endoligature is placed into an applicator which is introduced via a trocar bushing into e.g. the stomach cavity. The loop should be located completely within the applicator when entering into the stomach cavity. In the final position, the loop is then pushed out of the applicator using the knot-displacer. A fixation forceps is utilized to pull the material being ligated through the loop. Same is then placed at the desired location on the tissue and pulled securely close. This technique is e.g. suitable for the immediate sealing of a gall bladder perforation, for securing the base of the appendix during an appendectomy, or for sealing an opening in the peritoneum.

In the event that the ligature is to be applied prior to separation of a structure, one thread is threaded into the knot-displacer and then guided through an applicator and a trocar. Two needle carriers are required for this procedure. A first needle carrier is utilized to grasp the end of the thread for insertion of same via the application bushing and the trocar bushing. The end of the thread is then placed at the structure to be ligated using the needle carrier, grasped by a second needle carrier, guided around the structure, and passed back to the first needle carrier. The first needle carrier can then be used to pull the end of the thread back through the applicator to the outside. Following extracorporeal preparation, formation, and trimming of the knot, same is visually introduced using the knot-displacer to the location to be ligated where it is then pulled closed. After the knot is secured, the string is cut-off using a scissors.

The above described procedure can also be used to terminate a suture. Towards this end a conventional thread-needle-combination is utilized to perforate the desired tissue. Subsequent thereto, the knot is prepared extracorporeally and pulled closed at the tissue suture.

When it is not possible to prepare the required knot prior to an operation, the formation of the knot and its correct placement is extremely time consuming, at least for an unpractised surgeon. For this reason proper knot formation is not always assured. The knot slides poorly and if the knot is improperly applied the desired strength is not completely achieved.

It is therefore the underlying purpose of the invention to create a seal which constitutes a reliable substitute for a knot and which is quickly and easily established and easy to handle in both preoperative as well as intraoperative applications.

SUMMARY OF THE INVENTION

This purpose is achieved in accordance with the invention with a seal comprising a bushing and a thread one end of which is firmly connected to the bushing, and the bushing has at least one first lumen having a diameter which is larger then the diameter of at least one first axial lengthwise section of the thread, same having at least a second axial lengthwise section having enlargements formed along the axial extent thereof which are larger then the diameter of the first lumen. The seal in accordance with the invention has when e.g. used as a ligature securing mechanism, the advantage that it is both of simple construction and can also be positioned and closed using only reliable conventional knot-displacers. In the seal in accordance with the invention the enlargements formed in thread sections guarantee that the permanent sealing action first occurs in the last end section. The enlargements on the thread securely wedge at the inner surface of the first lumen to form a permanent sealing connection. The bushing is made from a material which is sufficiently flexible to facilitate deformation of the bushing under the application of force via the thread and, e.g. in the case of ligatures and tissue to be ligated, permanently compresses in the desired fashion and adapts suture tissue edges. In addition, the material from which the bushing is made has a sufficiently stable shape, at least in the vicinity of the inner surface of the first lumen, to only permit release of toothed engagement between the bushing and the enlargements of the thread in the event that the seal is forcibly destroyed. The inseparable connection between the enlargements of the thread and the bushing is achieved in a straight as well as in a bent bushing. The toothed engagement interaction is strengthened when the bushing is bent.

The thread of the seal in accordance with the invention is flexible and shape-stable to facilitate maintaining an opening of a previously prepared loop or for surrounding tissue to be ligated with the thread. The thread can be pushed into the bushing either extracorporeally or intracorporeally, since the first lumen directs the thread into the housing during insertion. Towards this end, additional simplification is achieved when the first lumen has e.g. a conical widened portion in the entrance region for the inserted thread. The other end of the thread is connected to the bushing. For example, the thread can be materially interlocked with the bushing at one end.

A plurality of enlargements are introduced on the thread according to need. Each of the enlargements comes into toothed engagement with the bushing when the seal is closed so that the seal is secured a plurality of times.

In a preferred embodiment of the invention, the bushing has a second lumen with a diameter which is larger then the diameter of a free end section of the thread.

This has the advantage that the thread and the bushing can be manufactured separately from each other and, if needed, differing materials can be combined for the bushing and thread. Using a bushing having two lumens, the one end of the thread is introduced and interlockingly connected to the bushing either in the second lumen or in the vicinity of a free end of the bushing in a material-induced, force-induced or shape-induced fashion. Economical and simple technical manufacture of the seal in accordance with the invention is facilitated by a two-lumen bushing.

In a preferred embodiment of the invention, the free end section is introduced sufficiently far into the second lumen of the bushing that the free end of the thread projects beyond a first end of the bushing and the free end has a swelling which is radially directed relative to the longitudinal axis of the thread and which is larger than the diameter of the second lumen.

This has the advantage that the thread can be permanently connected to the bushing using the simplest of means. The swelling can e.g. be embodied by a clip on the thread or the thread is cooled and/or heated on the end in such a fashion that a deformation in outer contour of the thread occurs to prevent pulling out the free end of the thread through the second lumen and out of the bushing without breaking the thread. In the event that the thread is introduced through the second lumen along the entire axial length of the bushing, the thread doubly supports bending of the bushing when sealing.

In further embodiments of the invention, the enlargements are disposed along the thread at narrow separations and the locations of maximum radial extent of the enlargements are rotated by 90° with respect to each other.

This has the advantage that toothed engagement occurs in the bushing around the periphery of the inner surface of the first lumen when closing the seal in accordance with the invention. The enlargements are preferentially rotated with respect to each other by 90°. They can, however, be disposed at differing angles with respect to each other if needed. The enlargements are either introduced on the outer surface of the thread or are shaped from the thread material by e.g. flattening the thread in the vicinity of an enlargement. In such an embodiment of the enlargements, the enlargements are formed from the thread material.

The thread material is preferentially selected in such a fashion that the swelling at one end of a thread can also be fashioned out of the thread material.

The thread and the bushing are preferentially made from plastic. This has the advantage that a plurality of differing and reliable materials can be used which have sufficient shape stability and strength for the desired application.

It is also possible, with the seal in accordance with the invention, to manufacture the bushing and the thread from an absorbable material. This has the advantage that the seal in accordance with the invention can be left inside the body and dissolves after a certain period of time following its insertion and placement.

The seal can be identified and its functionability checked from the outside if markings are introduced on the bushing and/or on the thread which are impervious to X-rays.

The seal in accordance with the invention can be manufactured for differing inner diameters. Towards this end the length of the bushing and its material thickness can be varied. When the seal in accordance with the invention is placed and closed, the thread can be cut-off in the vicinity of a second bushing end outside of the bushing.

The seal in accordance with the invention can also be utilized for ligations, in prefabricated ligation loops, or within the framework of a thread-needle combination for suturing. Use of the seal is not restricted to endoscopic surgery. Medical waste bags as well as non-medical objects can be permanently, quickly and simply securely bundled and captured with the seal described herein.

Further advantages can be derived from the description of the accompanying drawing. The above mentioned features and those to be described further below can be utilized in accordance with the invention individually or collectively in arbitrary combination. The embodiments mentioned are not to be considered as exhaustive enumeration rather have exemplary character.

The invention is shown in the drawing.

BRIEF DESCRIPTION OF THE DRAWING

FIG. 4 shows a seal in accordance with the invention having a loop size in preparation for pulling enlargements into a first lumen;

FIG. 5 shows a seal in accordance with the invention which is largely closed, and e.g. compresses or adapts a tissue not shown in the figure in a desired fashion;

FIG. 6 shows a thread section of a seal in accordance with the invention having enlargements which are rotated with respect to each other.

DESCRIPTION OF THE PREFERRED EMBODIMENT

Figure 1:
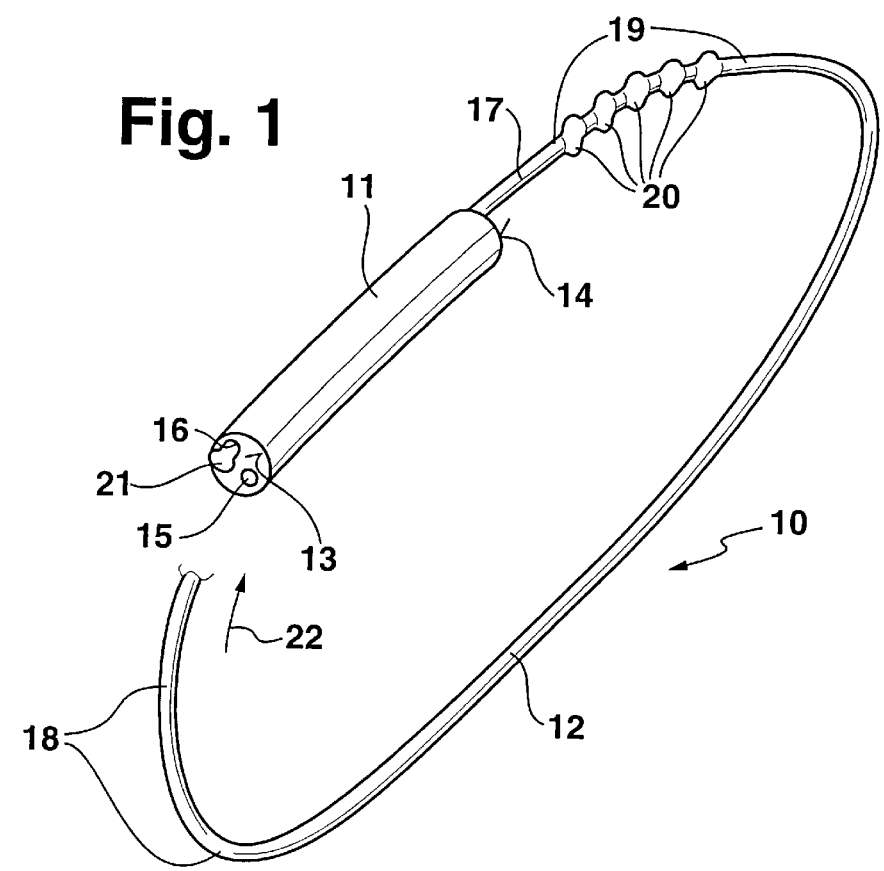
FIG. 1 shows a seal in accordance with the invention in an open state and can be utilized as a ligature in this form.

The individual figures of the drawing show the object in accordance with the invention in a highly schematic fashion and should not be taken to scale. The individual objects of the seal in accordance with the invention are at least partially shown magnified so that their construction and function can be more easily illustrated.

FIG. 1 shows a seal 10 consisting essentially of a bushing 11 and a thread 12. The bushing 11 and the thread 12 can be manufactured from a flexible metal or from a flexible fibre-reinforced material. In the embodiment of FIG. 1, both the bushing 11 as well as the thread 12 are manufactured from a tissue-compatible plastic material which is both flexible as well as sufficiently stable in shape. The bushing 11 has a first bushing end 13 and second bushing end 14. A first lumen 15 and a second lumen 16 are formed along the bushing 11. The first lumen 15 and the second lumen 16 extend along the entire axial length of the bushing 11. The lumina 15, 16 are dimensioned in such a fashion that at least partial sections of the thread 12 can be introduced into and threaded through the lumina 15, 16.

The thread 12 is manufactured from a single material along its entire length and has longitudinal sections which are differently configured. A first axial lengthwise section 18 is dimensioned in such a fashion that it can be passed through the first lumen 15 when required. A second axial lengthwise section 19 is likewise formed on the thread 12 having enlargements 20 which are radially larger than the first lumen 15. A free end section 17 of the thread 12 is introduced into the second lumen 16 and its free end projects out of the bushing 11 beyond the first end of the bushing 13. A swelling 21 is formed on the tip of the thread 12 to prevent the end of the thread 12 from being able to be pulled through the bushing 11 with its end swelling 21. The swelling 21, which can be produced by deformation of the thread material or via a clip which is screwed into or clamped on the thread 12, holds the thread 12 in the bushing 11. The other end of the thread can be inserted into the first lumen 15 in the direction of arrow 22. The first lumen 15 thereby guides the thread 12 through the bushing 11 in a directed and stable fashion. The thread 12 can be pushed forward far beyond the second end of the bushing 14. The lengthwise section 18 can also be provided with a needle on the end for perforating tissue or other materials.

Figure 2:
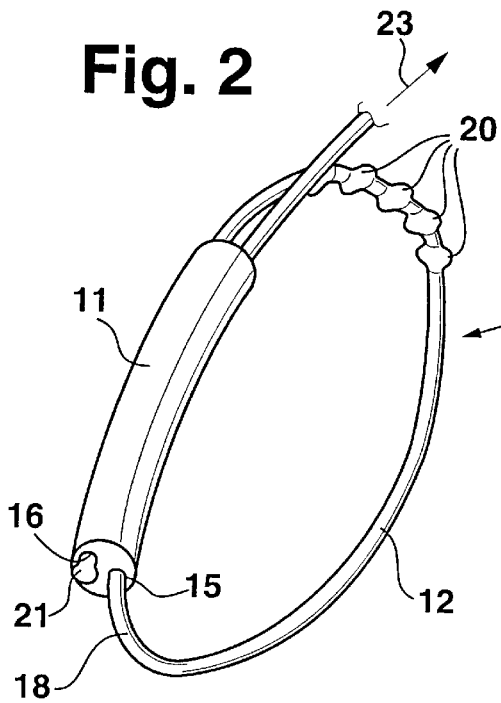
FIG. 2 shows a seal in accordance with the invention in the form of a prefabricated ligature loop.

FIG. 2 shows the seal 10 in the form of a prefabricated ligature loop or the seal 10 of FIG. 1 for closing the ligature. In the position shown, the seal 10 forms a loop which is self-supported in the open position. A material e.g. to be ligated can be pulled through the opening in the loop. It is, however, also possible to first direct the thread 12 around tissue which is to be ligated and subsequently insert same into the bushing 11. In the event that the seal 10 is formed in the manner shown in FIG. 2, the swelling 21 prevents this end of the thread 12 from being pulled through the bushing 11. The swelling 21 holds the thread 12 in a fixed position in the second lumen 16. The thread 12 can travel without the expenditure of force in the direction of arrow 23 along the entire first lengthwise section in the first lumen 15. In the configuration of the loop shown in the figure, movement of the thread is also possible in opposition to the direction of arrow 23.

Figure 3:
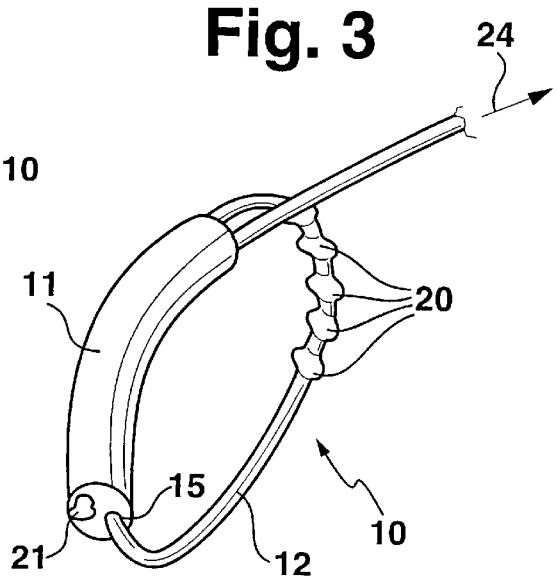
FIG. 3 shows a seal in accordance with the invention having a reduced loop.

FIG. 3 shows the seal 10 already shown in FIG. 2 in a position in which the thread 12 is further positioned in the direction of arrow 24. The bushing 11 is somewhat curved and is adapted to a loop radius. The other end of the thread 12 having the terminal swelling 21 is permanently attached to the bushing 11 via the swelling 21 and the enlargements 20 move towards the first lumen 15.

FIG. 4 shows a further representation of the seal 10, wherein the thread 12 has been pulled to a further extent in the direction of arrow 25. The first enlargements 20 have penetrated into the first lumen 15. The bushing 11 itself is curved to a further extent and approaches tissue which is to be ligated. The terminal swelling 21 is wedged in the second lumen 16 so that the thread 12 is securely fixed in the second lumen 16.

FIG. 5 shows the seal 10 in a nearly closed state. The thread 12 has moved further in the direction of arrow 26 and the enlargements 20 have already penetrated into the first lumen 15 with the exception of one enlargement 20. The bushing 11 is curved to an even further extent and the swelling 21 has wedged itself more firmly into the second lumen 16. The seal 10 is closed when enlargements 20 are pulled into the first lumen 15.

FIG. 6 shows a section of a thread 12 which can be utilized in connection with the seal 10 of FIGS. 1 through 5. Enlargements 27 and 28 are arranged at 90° with respect to each other along the plastic thread 12. The enlargements 27 and 28 are formed from the thread material by flattening the thread at these locations. The flattening causes a radial enlargement which interferes, when closing the ligature binder, with the dimensions of the first lumen 15 in such a fashion that the enlargements 27 and 28 effect a connection to the seal bushing which can only be forcibly re-opened.

A seal 10 comprises a bushing 11 and a thread 12, wherein the bushing 11 has a first lumen 15 and a second lumen 16. The lumina 15 and 16 extend along the entire length of the bushing 11. The thread 12 can be introduced at one end into the second lumen 16 and has a swelling 21 at the free end which prevents reintroduction and travel of the end of the thread through the second lumen 16. The thread 12 can be introduced into the first lumen 15 via its other free end and pushed through first lumen 15. Enlargements 20 are formed on the thread 12 having a size preventing introduction into the first lumen 15 without the exercise of force. The bushing 11 and the thread 12 are manufactured from a flexible material having a stable shape. When the enlargements 20 are pulled into the first lumen 15, the bushing 11 bends and seats on e.g. tissue to be ligated. When the enlargements 20 are completely pulled into the first lumen 15, the seal 10 is permanently closed. Subsequent thereto the thread 12 is cut-off outside of the seal 10. The seal 10 can be applied using conventional knot-displacers.

We claim:

1. A seal comprising:

a bushing made from a flexible material and having a first lumen with a first lumen diameter, said bushing also having a second lumen with a second lumen diameter; and a thread having a free end section with a diameter smaller than said second lumen diameter, said free end section passing through said second lumen, said free end section having an end securely connected to said bushing, said thread also having a first length with a diameter smaller than said first lumen diameter and said thread having a second length with enlargements, said enlargements having a diameter larger than said first lumen diameter, wherein said bushing deforms under the application of a force caused by said thread when said first length is pulled through said first lumen.

2. The seal of claim 1, wherein said free end section is disposed sufficiently far into said second lumen that said end of said thread projects beyond a first bushing end, said end having a swelling transverse to a longitudinal axis of said thread which is larger than said second lumen diameter.

3. The seal of claim 2, wherein said swelling is formed in a thread material.

4. The seal of the claim 1, wherein said enlargements are disposed along said thread in a row at narrow separations from each other, and neighboring enlargements are rotated with respect to each other by 90°.

5. The seal of claim 1, wherein said second length enlargements are formed in a thread material.

6. The seal of claim 1, wherein said thread and said bushing are manufactured from plastic.

7. The seal of claim 1, wherein said bushing and said thread are manufactured from an absorbable material.

8. The seal of claim 1, wherein at least one of said bushing and said thread have markings impervious to X-rays.

* * * * *